US008834751B2

(12) United States Patent
Dittmann et al.

(10) Patent No.: US 8,834,751 B2
(45) Date of Patent: Sep. 16, 2014

(54) SYSTEM AND METHOD FOR SINTERING DENTAL RESTORATIONS

(75) Inventors: Rainer K. Dittmann, München (DE); Anthony A. Bredebusch, Landsberg am Lech (DE); Christian A. Richter, Feldafing (DE); Anja B. Fischer, Seefeld-Hechendorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 93 days.

(21) Appl. No.: 13/147,614

(22) PCT Filed: Mar. 10, 2010

(86) PCT No.: PCT/US2010/026745
§ 371 (c)(1),
(2), (4) Date: Aug. 3, 2011

(87) PCT Pub. No.: WO2010/104901
PCT Pub. Date: Sep. 16, 2010

(65) Prior Publication Data
US 2011/0309540 A1 Dec. 22, 2011

Related U.S. Application Data

(60) Provisional application No. 61/159,637, filed on Mar. 12, 2009.

(51) Int. Cl.
*B29C 67/04* (2006.01)
*A61C 13/00* (2006.01)
*F27D 5/00* (2006.01)
*A61C 13/12* (2006.01)

(52) U.S. Cl.
CPC .......... *F27D 5/0043* (2013.01); *A61C 13/0003* (2013.01); *A61C 13/12* (2013.01)
USPC .............................................. 264/16; 264/51

(58) Field of Classification Search
USPC ............................................................ 264/16
See application file for complete search history.

(56) References Cited

U.S. PATENT DOCUMENTS 3,589,694 A * 6/1971 Gelling et al. ................ 432/261
D221,745 S 9/1971 Holdredge
(Continued)

FOREIGN PATENT DOCUMENTS

DE 10052203 A1 4/2001
JP 3-296006 12/1991
(Continued)

OTHER PUBLICATIONS

"Lava 200™ Furnace 200, Faster sintering made easy", 3M ESPE, St. Paul, MN, USA [on line], retrieved from the internet prior to Mar. 12, 2009. URL <http://solutions.3m.com/wps/portal/3M/en_US/3M-ESPE/dental-professionals/products/category/cad-cam/lava-furnace-200/>, pp. 12.

(Continued)

Primary Examiner — Larry Thrower
Assistant Examiner — Xue Liu
(74) Attorney, Agent, or Firm — Nicole J. Einerson (57) ABSTRACT

A system and method for sintering dental restorations. The system can include a monolithic sintering support comprising a surface, and at least one dental restoration positioned in direct contact with the surface of the monolithic sintering support. The method can include providing a monolithic sintering support comprising a surface, positioning a dental restoration in direct contact with the surface, and sintering the dental restoration while the dental restoration is in direct contact with the surface of the monolithic sintering support to form a sintered dental restoration.

20 Claims, 6 Drawing Sheets

(56) References Cited

U.S. PATENT DOCUMENTS

| | | | |
|---|---|---|---|
| 3,959,002 A * | 5/1976 | Esper | 501/129 |
| 4,184,840 A | 1/1980 | Gamberg | |
| D256,273 S | 8/1980 | Townsend | |
| 4,348,176 A | 9/1982 | Gamble | |
| 4,405,300 A * | 9/1983 | Lubowsky et al. | 432/2 |
| D307,462 S | 4/1990 | Merkouris | |
| 4,925,561 A | 5/1990 | Ishii | |
| 5,415,775 A * | 5/1995 | Castillon et al. | 210/490 |
| 5,993,970 A | 11/1999 | Oscarsson | |
| D476,725 S | 7/2003 | Dushek | |
| 6,709,694 B1 | 3/2004 | Suttor | |
| 6,756,421 B1 | 6/2004 | Todo | |
| D544,949 S | 6/2007 | Winters | |
| D571,608 S | 6/2008 | Yeung | |
| 7,624,688 B2 | 12/2009 | Kulbeth | |
| D628,266 S | 11/2010 | Dittmann | |
| D628,267 S | 11/2010 | Dittmann | |
| D628,268 S | 11/2010 | Dittmann | |
| D628,269 S | 11/2010 | Dittmann | |
| D628,673 S | 12/2010 | Dittmann | |
| D628,674 S | 12/2010 | Dittmann | |
| 2002/0076530 A1 * | 6/2002 | MacDougald et al. | 428/195 |
| 2002/0184922 A1 | 12/2002 | Dick | |
| 2006/0018780 A1 | 1/2006 | Hosamani | |
| 2006/0082033 A1 | 4/2006 | Hauptmann | |
| 2006/0117989 A1 | 6/2006 | Hauptmann | |
| 2008/0199823 A1 | 8/2008 | Miller | |
| 2008/0286718 A1 | 11/2008 | Franke | |
| 2011/0039221 A1 | 2/2011 | Hanzawa | |

FOREIGN PATENT DOCUMENTS

| | | |
|---|---|---|
| SU | 1699982 | 12/1991 |
| WO | WO 97/07078 | 2/1997 |
| WO | WO 2008/098157 | 8/2008 |

OTHER PUBLICATIONS

"Fabrication of Kiln Furniture with Variable Geometry Especially for Technical Ceramics", Kollenberg, Wolfgang and Nikolay, Dieter; Werkstoffzentrum Rheinbach GmbH, Lise-Meitner-Strasse 1, 53359 Rheinbach, [on line], retrieved from the internet prior to Mar. 12, 2009. URL <http://www.werkstoffzentrum.de>, pp. 5.

"Realisierung Keramischer Prototyping mittels 3D-Druck and Heißgießen", Kindtner et al., Werkstoffzentrum Rheinbach GmbH, Lise-Meitner-Str. 1, 53359 Rheinbach [on line]. retrieved from the internet prior to Mar. 12, 2009. URL http://www.werkstoffzentrum.de, pp. 9.

International Search Report dated May 13, 2010, for PCT/US2010/26745, 3 pages.

* cited by examiner

SYSTEM AND METHOD FOR SINTERING DENTAL RESTORATIONS

CROSS REFERENCE TO RELATED APPLICATIONS

This is a national stage filing under 35 U.S.C. 371 of PCT/US2010/026745, filed Mar. 10, 2010, which claims priority to U.S. Provisional Application No. 61/159,637, filed Mar. 12, 2009, the disclosure of which is incorporated herein by reference in its entirety.

FIELD

The present disclosure is generally directed to a system and method for sintering ceramic articles, and particularly, for sintering dental restorations.

BACKGROUND

Because of their physical properties, ceramics can be good candidates for use in the construction of high-quality pre-shaped dental restorations. Aluminum oxide (sometimes referred to as "alumina") and zirconium oxide (sometimes referred to as "zirconia") ceramics have been used in the dental field because of their physical and aesthetic properties.

In some existing systems, ceramic dental restorations can be produced by means of a computer-aided design (CAD) system that function in conjunction with a computer-integrated manufacturing (CIM) system. Such a CIM system is available, for example, under the trade designation LAVA™ from 3M ESPE AG (Seefeld, Germany). The CAD system can be coupled to an optical scanner and a numerically-controlled (NC)-milling machine. The optical scanner can be configured to capture a three-dimensional surface of a dentition impression and send the captured data to the CAD system. With the CAD system, a user can modify the surface data as desired, calculate computer numerically-controlled (CNC) data from the shape data using computer-aided manufacturing (CAM) software, and then send the corresponding CNC data to the NC-milling machine. The NC-milling machine can then mill a zirconium oxide (or zirconia) ceramic blank in an as precise as possible agreement with the shape data. Finally, the milled ceramic blank can be sintered, for example, in a sintering furnace.

During the sintering process, the ceramic material generally shrinks a certain amount. In some systems, ceramic dental restorations (e.g., bridge frameworks) can be positioned on pegs, pins or rods (e.g., formed of alumina), or suspended from hangers (e.g., formed from a platinum alloy) during sintering. Such pegs, pins, rods, or hangers can be placed on a honeycomb-like sintering tray in order to accommodate the dental restoration geometry. Such an arrangement allows for any linear movement of the dental restoration that may be induced by shrinkage. In other systems, ceramic dental restorations can be placed on ceramic beads or balls, or on ceramic bulk material, which can then be placed in or on a container or support for sintering.

SUMMARY

Some aspects of the present disclosure provide a method for sintering dental restorations. The method can include providing a monolithic sintering support comprising a surface, positioning a dental restoration in direct contact with the surface, and sintering the dental restoration while the dental restoration is in direct contact with the surface of the monolithic sintering support to form a sintered dental restoration.

Some aspects of the present disclosure provide a use of a monolithic sintering support for sintering dental restorations, and particularly, the use of a surface of a monolithic sintering support for positioning dental restorations for sintering. For example, in some embodiments, the monolithic sintering support is characterized by including at least 97 wt % alumina. In some embodiments, the monolithic sintering support is characterized by including at least a porosity of at least about 25%. In some embodiments, the surface of the monolithic sintering support is characterized by including or being defined by recesses in which one or more dental restorations can be positioned during sintering.

Some aspects of the present disclosure provide a system for sintering dental restorations. The system can include a monolithic sintering support comprising a surface, and at least one dental restoration positioned in direct contact with the surface of the monolithic sintering support. In some embodiments, the surface includes or is defined by at least one recess, and the at least one dental restoration can be positioned at least partially in the at least one recess. In some embodiments, the monolithic sintering support is characterized by including at least 97 wt % alumina. In some embodiments, the monolithic sintering support is characterized by including at least a porosity of at least about 25%.

Other features and aspects of the present disclosure will become apparent by consideration of the detailed description and accompanying drawings.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a system and method for sintering dental restorations. In general, a sintering system of the present disclosure can include a sintering support or tray, and one or more dental restorations positioned directly on the support for sintering while avoiding distortion, discoloration, decoloration (e.g., of shaded restorations), and/or adhesions of the dental restorations. In some embodiments, the sintering support can be formed of alumina and the dental restorations can be formed of zirconia. In some embodiments, the method for sintering dental restorations can include positioning the dental restorations directly on the sintering support.

In some existing systems, ceramic dental restorations (e.g., bridge frameworks) can be positioned on pegs, pins or rods (e.g., formed of alumina), or suspended from hangers (e.g., formed from a platinum alloy) during sintering. Some dental restorations, such as partial crowns, can be difficult to handle, balance on pins, and/or suspend from hangers. In some existing systems, interactions between the dental restoration and the sintering support can be difficult to control. For example, in some systems, bulk or beaded material on which dental restorations are positioned, can be sinter-active and can become sintered itself, and/or can become sintered to the dental restoration. Furthermore, drying of colored or shaded dental restorations can be difficult in existing systems where proper air circulation is not available, which can result in accumulation of coloring agents on the dental restoration, leading to an aesthetically poor or unusable dental restoration. Moreover, not only are the pegs, pins, rods and suspension systems of existing systems cumbersome for handling and positioning the dental restorations, but arranging and mapping a large number of restorations in the existing systems can also be cumbersome or impossible, and can require tedious and time-consuming sorting of dental restorations following the sintering process.

Figure 1:
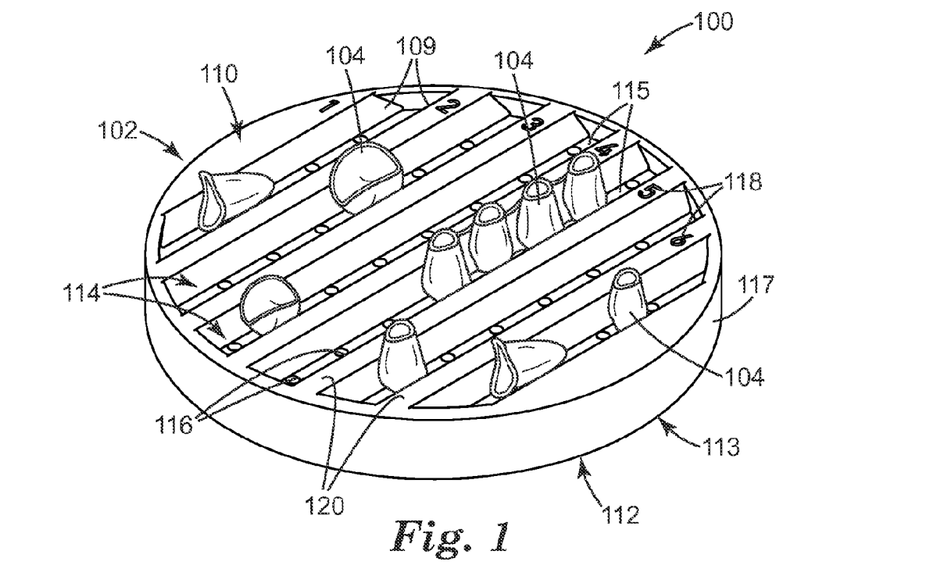
FIG. 1 is a perspective view of a sintering system according to one embodiment of the present disclosure, the sintering system comprising a sintering support and dental restorations positioned on the sintering support.
Figure 2:
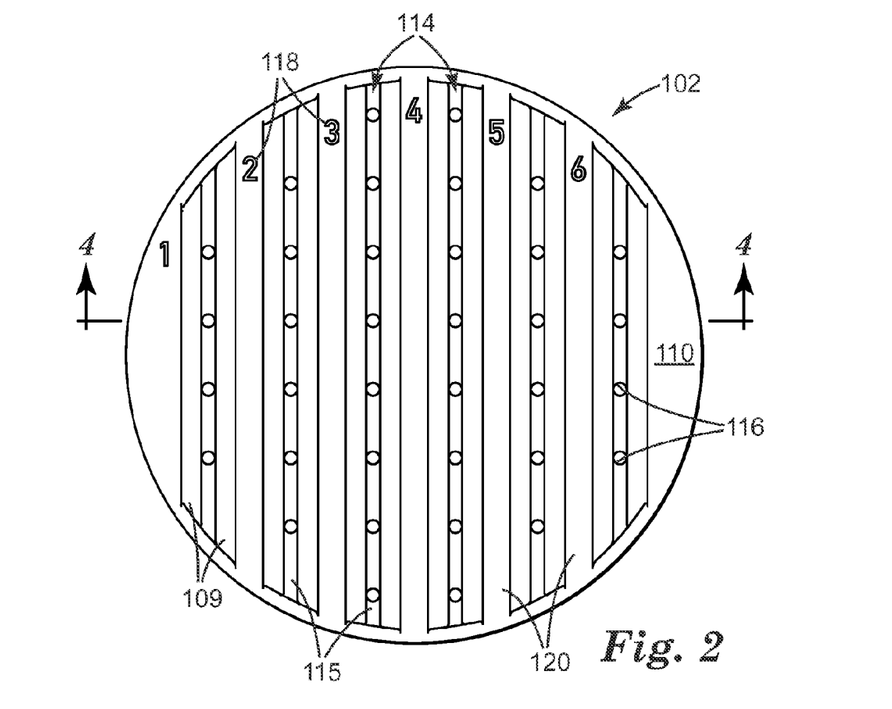
FIG. 2 is a top view of the sintering support of FIG. 1.
Figure 3:
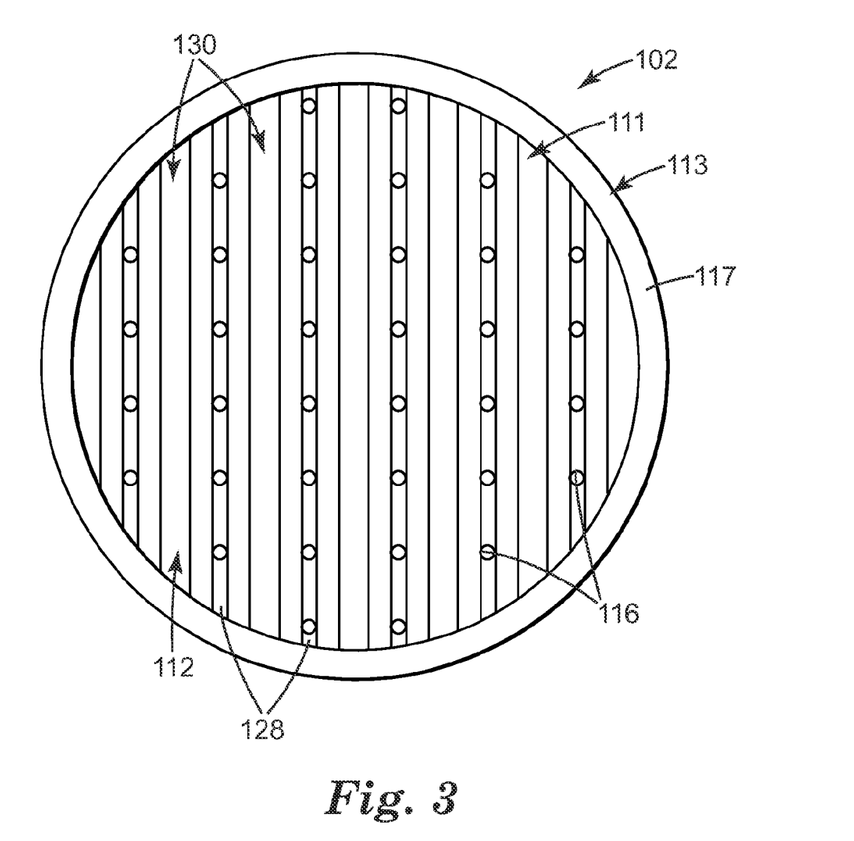
FIG. 3 is a bottom view of the sintering support of FIGS. 1-2.
Figure 4:
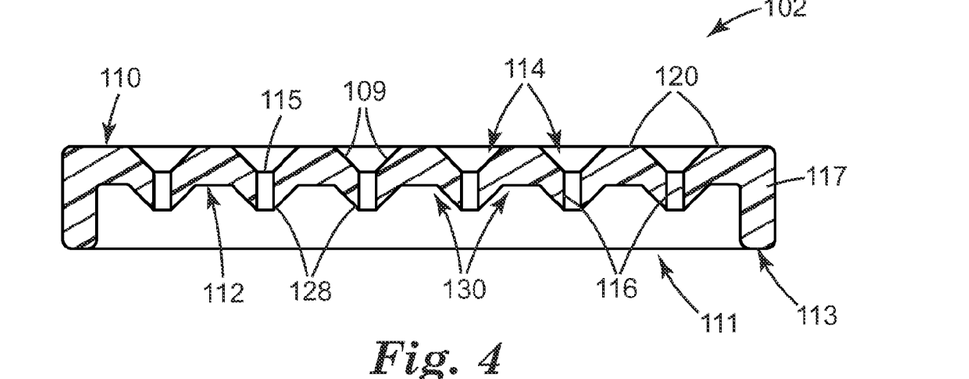
FIG. 4 is a cross-sectional side view of the sintering support of FIGS. 1-3, taken along line 4-4 of FIG. 2.

FIG. 1 illustrates a sintering system 100 according to one embodiment of the present disclosure. As shown in FIG. 1, the sintering system 100 can include a sintering support or tray 102 (and particularly, a monolithic sintering support 102, and more particularly, a monolithic ceramic sintering support 102), and one or more dental restorations 104 (and particularly, ceramic dental restorations 104) positioned on the sintering support 102. FIGS. 2-4 illustrate alternate views of the sintering support 102. For clarity, only a few dental restorations 104 are illustrated in FIG. 1; however, it should be understood that dental restorations 104 can be positioned on the sintering support 102 at a higher packing density, and many more dental restorations 104 can be positioned on the sintering support 102 at one time to increase productivity.

The phrases "dental restoration" and "ceramic dental restoration" are generally used to refer to any ceramic article that can be used in the dental field, including, but not limited to, crowns, partial crowns, inlays, onlays, abutments, bridges (e.g., including 2-part, 3-part, 4-part, 5-part or 6-part bridges), other suitable dental articles, and combinations thereof. The dental restoration can include a three-dimensional inner and outer surface including convex and concave structures. Compared to other ceramic articles, such as pottery or paving stones, dental restorations can be relatively small and can include filigree. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm. In some embodiments, the dental restoration can comprise or consist essentially of a glass; glass ceramic; polycrystalline ceramic material comprising alumina (e.g., $Al_2O_3$), zirconia ($ZrO_2$), partly or fully stabilized zirconia (e.g., Yttrium-stabilized zirconia), titanium dioxide ($TiO_2$), high-strength oxides of the elements of the main groups II, II and IV and the subgroups III and IV, and their mixtures, and combinations thereof. As described in greater detail below, in some embodiments, the dental restorations are shaded or colored to provide the desired aesthetics, which are generally referred to herein as "shaded dental restorations."

In some embodiments, the sintering support 102 can comprise or consist essentially of a glass; glass ceramic; polycrystalline ceramic material comprising alumina (e.g., $Al_2O_3$), zirconia ($ZrO_2$), partly or fully stabilized zirconia (e.g., Yttrium-stabilized zirconia), titanium dioxide ($TiO_2$), high-strength oxides of the elements of the main groups II, II and IV and the subgroups III and IV, and their mixtures, and combinations thereof. However, as described in greater detail below, in some embodiments, the material purity (e.g., minimal contaminants or impurities) of the sintering support 102 can be important in effectively sintering the dental restorations 104.

As shown in FIGS. 1-4, and with particular reference to FIG. 4, the sintering support 102 can include a first, top surface 110, and a second, bottom surface 112. While a variety of shapes and structures of the sintering support 102 are possible, the second surface 112 of the embodiment illustrated in FIGS. 1-4 (and as particularly shown in FIGS. 3 and 4) includes a raised or recessed portion, or has a generally concave shape, such that the sintering support 102 (and the second surface 112) includes an inner portion 111 that is raised relative to an outer portion 113. Said another way, at least a portion of the sintering support 102 (and the second surface 112) is raised relative to a surface on which the sintering support 102 is resting. As shown in FIG. 4, the outer portion 113 can include a flange 117 that extends downwardly relative to the inner portion 111 and which defines the lowermost portion of the second surface 112. By employing such a raised inner portion 111, in some embodiments, the sintering support 102 can achieve more uniform air circulation through sintering support 102 and around the dental restorations 104 positioned thereon during sintering, as well as during an optional drying process described in greater detail below. Such air circulation can be important in the field of making dental restorations.

As shown in FIGS. 1-4, the sintering support 102 can further include one or more recesses or depressions 114, such that at least a portion of the first surface 110 is defined by the one or more recesses 114. As shown in FIG. 1, the dental restorations 104 can be positioned on the first surface 110, and particularly, in direct contact with the first surface 110, for sintering. Particularly, the dental restorations 104 can be positioned at least partially in the one or more recesses 114, and more particularly, in direct contact with the one or more recesses 114. As shown in FIGS. 1, 2, and 4, in some embodiments, each recess 114 can be defined by one or more sidewalls 109 and a base 115. In some embodiments, the dental restorations 104 can be positioned in direct contact with at least one of the sidewalls 109 and base 115. By way of example only, each recess 114 illustrated in FIGS. 1-4 includes two angled sidewalls 109 and a flat base 115. A variety of types of dental restorations 104 are shown in FIG. 1 by way of example only. A bridge is shown as being positioned within one recess 114. However, it should be understood that larger dental restorations 104 can be positioned on the sintering support 102 in such a way that they span more than one recess 114.

By way of example only, the dental restorations 104 are shown primarily in FIG. 1 with the occlusal surfaces of the dental restorations 104 facing downwardly (i.e., toward the bottom of the recesses 114). However, it should be understood that the dental restorations 104 can be positioned in a variety of orientations on the sintering support 102, depending on the material makeup and configuration of the dental restorations 104.

By way of example only, the sintering support 102 illustrated in FIGS. 1-4 includes six recesses 114, and by way of further example, the recesses 114 extend along a length of the sintering support 102, such that the recesses 114 in the embodiment illustrated in FIGS. 1-4 are in the form of channels, or elongated grooves. The sintering support 102 illustrated in FIGS. 1-4 is shown as being round or circular, and the recesses 114 are shown as extending from one side of the sintering support 102 to another. Due to the circular shape of the sintering support 102, the recesses 114 toward the center of the sintering support 102 are longer than the recesses 114 positioned further away from the center. The shape of the sintering support 102 and the arrangement of the recesses 114 are shown by way of example only. It should be understood, however, that the sintering support 102 can be formed into a variety of shapes and sizes to accommodate a variety of furnaces that are configured to sinter dental restorations. For example, in some embodiments, the first surface 110 of the sintering support 102 can have an area of no greater than about 300 cm$^2$, in some embodiments, no greater than about 150 cm$^2$, and in some embodiments, no greater than about 50 cm$^2$. In addition, a variety of recess arrangements can be employed, particularly, recess arrangements that facilitate indexing the locations of the dental restorations 104 on the sintering support 102.

In some embodiments, the sintering support 102 can include an indexing system. For example, as shown in FIGS. 1 and 2, in some embodiments, the sintering support 102 can include an indexing system that includes a series of recess identifications 118. By way of example only, the recess identifications 118 are illustrated in FIGS. 1 and 2 as Arabic numerals (i.e., "1" through "6"), which assign a number to each recess 114. The recess identifications 118 are shown as being provided on the first surface 110, so that the recess identifications 118 are easily visible during handling of the sintering support 102. However, it should be understood that the recess identifications 118 can be positioned in a variety of locations or on a variety of surfaces of the sintering support 102. The recess identifications 118 can include a variety of markings, numbering, and/or other identification insignia that can facilitate indexing the locations of the dental restorations 104 and can greatly reduce the time required to locate and retrieve a given dental restoration 104 following the sintering process. Additional identifications (e.g., markings, numberings or other identifications) can be used to index other loci in the recesses 114 (e.g., loci along the length of a recess 114) to facilitate even more accurate positioning and indexing of the dental restorations 104.

The sintering support 102 can allow for faster and more efficient placement and retrieval of the dental restorations 104, and can also allow for a higher packing density of dental restorations 104 during sintering. As a result, the sintering support 102 can improve the productivity of a dental lab, both in terms of the number of dental restorations that can be produced per unit time, but also in reducing or eliminating tedious and time-consuming identification or sorting procedures.

As mentioned above, in some embodiments, each recess 114 can be defined by two angled sidewalls 109 and a flat base 115. As a result, in some embodiments, each recess 114 can include a truncated V cross-sectional shape, such that each recess 114 has a length that extends along the sintering support 102, and a width that varies with the depth of the recess 114. That is, each recess 114 includes a dimension (i.e., the width) that varies in the direction of another dimension (i.e., the depth). Particularly, in the embodiment illustrated in FIGS. 1-4, the width of each recess 114 is widest at its top, decreases as the depth of each recess 114 increases, and is narrowest at its base 115.

Such a truncated V cross-sectional shape and/or decreasing width of the recess 114 can allow the recess 114 to accommodate any shrinkage of the dental restoration(s) 104 that may occur during sintering, and ensures that the dental restoration(s) 104 will remain in contact with at least a portion of the recess 114 (e.g., at least one of the sidewalls 109 and base 115) during the sintering process. The shape of the recess 114 can allow the dental restoration(s) 104 to slide down in the recess 114 as the dental restoration(s) 104 shrink during sintering. In addition, the shape of the recess 114 can inhibit dislocation of the dental restoration(s) 104 during handling of the sintering support 102.

The flat base 115 of the recess 114 can reduce the number of sharp peaks, corners and edges in the sintering support 102, to provide stress relief and inhibit cracking and crack propagation in the sintering support 102 during the thermal expansion and contraction that may occur during the firing or sintering step of the dental restoration(s) 104.

In some embodiments, as shown in FIG. 4, each recess 114 can be separated from an adjacent recess 114 by a separating wall, rib or protrusion 120, the top surface of which can define at least a portion of the first surface 110 of the sintering support 102. As shown in FIGS. 1 and 2, the top surface of the separating wall(s) 120 can also provide a substrate or surface for the recess identifications 118. As shown in FIGS. 3 and 4, the sintering support 102 can further include one or more downwardly-projecting walls, ribs, or protrusions 128 that correspond to the base(s) 115 of the recesses 114. In addition, each downwardly-projecting wall 128 is shown as being separated by one or more upwardly-extending recesses 130, each of which corresponds to the position of a separating wall 120. The recesses 114 and walls 120 can define at least a portion of the first surface 110 of the sintering support 102, and the walls 128 and recesses 130 can define at least a portion of the second surface 112, and particularly at least a portion of the inner portion 111 of the second surface 112.

With continued reference to FIGS. 1-4, and with particular reference to FIG. 4, the sintering support 102 can include one or more apertures 116 positioned to provide fluid communication between the first surface 110 and the second surface 112. As described in greater detail below, such apertures 116 can facilitate uniform drying of shaded or colored dental restorations 104, uniform air and heat circulations around the dental restorations 104, and can inhibit distortion, discoloration, and/or decoloration (e.g., of shaded dental restorations) of the dental restorations 104.

The recesses 114 illustrated in FIGS. 1-4 can provide the advantages described above. However, it should be understood that other recess shapes are also possible and suitable for inhibiting dislocation of the dental restorations 104 during handling of the sintering support 102 and for accommodating any shrinkage of the dental restorations 104 during sintering.

In general, the sintering support 102 is substantially inert at high temperatures. As a result, there is generally little to no chemical reaction between the sintering support 102 and the dental restorations 104 (and particularly, dental restorations 104 formed of zirconia); there is minimal to no sintering activity of the sintering support 102; and there is minimal to no release of coloring ions (e.g., impurities) from the sintering support 102 into the dental restorations 104, resulting in no observable (i.e., by the naked human eye) discoloration of the dental restorations 104. Furthermore, the sintering support 102 can have a porous structure and high surface roughness to reduce the contact area with the dental restorations 104 when the dental restorations 104 are positioned directly on the first surface 110 of the sintering support 102. The porosity also enables uniform drying of shaded dental restorations.

A variety of methods can be employed to produce a sintering support 102 of the present disclosure, with a defined amount or range of porosity. In some embodiments, the sintering support 102 is prepared by pressing technology, which can include axial or isostatically pressing of ceramic (e.g., alumina) powders, granules, fibers or mixtures with or without pressing additives (e.g. polyvinylalcohol, polyethyleneglycol) in a die of a desired shape. The porosity of the sintering support 102 can be controlled by adjusting the pressing conditions (e.g. pressing pressure). To obtain a controlled porosity or pore structure, organic additives (e.g. polymeric beads or fibers) can additionally be added to the powder mixture. After pressing, the pressed article is fired to burn out the organic components and to sinter the compacted powder, leaving behind open spaces to achieve the desired porosity in the sintering support 102.

In some embodiments, the sintering support 102 can be formed by slip casting of a ceramic slurry. In such embodiments, a ceramic slurry based on aqueous or organic solvents containing liquefier, binder and other surfactants can be cast into a porous mould of desired shape. The solvent can be soaked into the porous mould and a green ceramic body can be formed. The green ceramic body can then be demolded, and the organics can be removed during debinding and firing of the ceramic body. Addition of organic additives (e.g. polymeric beads or fibers) into the ceramic slurry can achieve the desired porosity, as described above with respect to pressing technology.

In some embodiments, the sintering support 102 can be formed by injection die molding (e.g., with a cold or warm plastic paste). In such embodiments, cold plastic feedstocks (e.g. starches, cellulose or alginates as binder) or warm plastic feedstocks (e.g. based on waxes or polyolefins, e.g., polyethylene (PE) and/or polypropylene (PP)) can be pressed by a piston or extruder into the mold. A desired porosity can be obtained by addition of organic additives (e.g. polymeric beads or fibers) into the ceramic paste, as described above with respect to slip casting. After debinding and firing, the porosity can be maintained in the resulting (i.e., sintered) sintering support 102.

In some embodiments, the sintering support 102 can be formed by a three-dimensional printing build-up process, sometimes referred to as "rapid prototyping" or "solid freeform fabrication." In such embodiments, a loose layer of ceramic particles can be locally fixed by printing a suitable binder system into the powder bed. The desired shape can be built-up layer by layer altering the fixation step and dosing thin powder layers. After the printing process, the binder can be allowed to harden, and the resulting sintering support 102 can be removed from the powder bed. In some embodiments, the porosity of the resulting sintering support 102 can be controlled by using powders or powder mixtures of different particle size. After removal of the binder system, the part can be sintered.

As mentioned above, the material makeup and structure of the sintering support 102 can allow for the dental restorations 104 to be positioned in direct contact with the first surface 110 of the sintering support 102. That is, in some embodiments, the dental restorations 104 can be positioned on the sintering support 102 without the need for any additional support structures, such as pins, pegs, hangers, or the like, or without the need for separating media (e.g., powder) between the dental restorations 104 and the sintering support 102.

Figure 5:
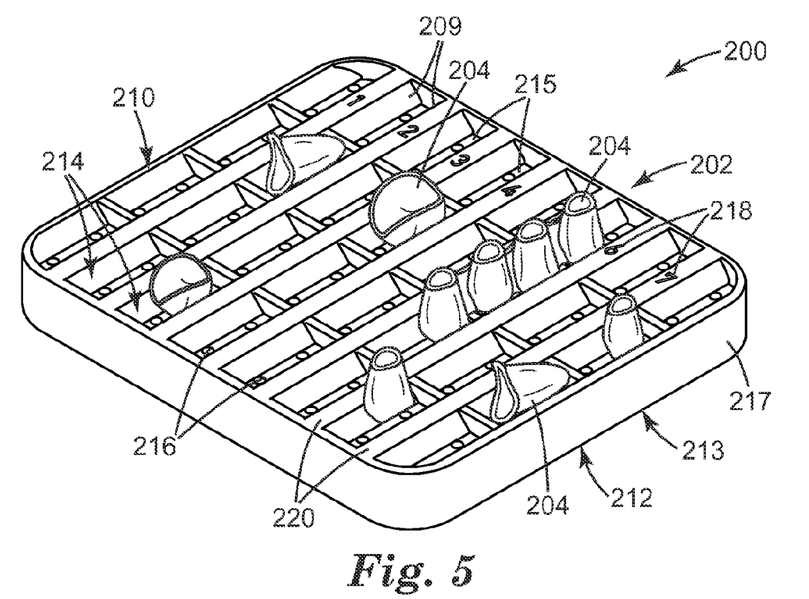
FIG. 5 is a perspective view of a sintering system according to another embodiment of the present disclosure, the sintering system comprising a sintering support and dental restorations positioned on the sintering support.
Figure 6:
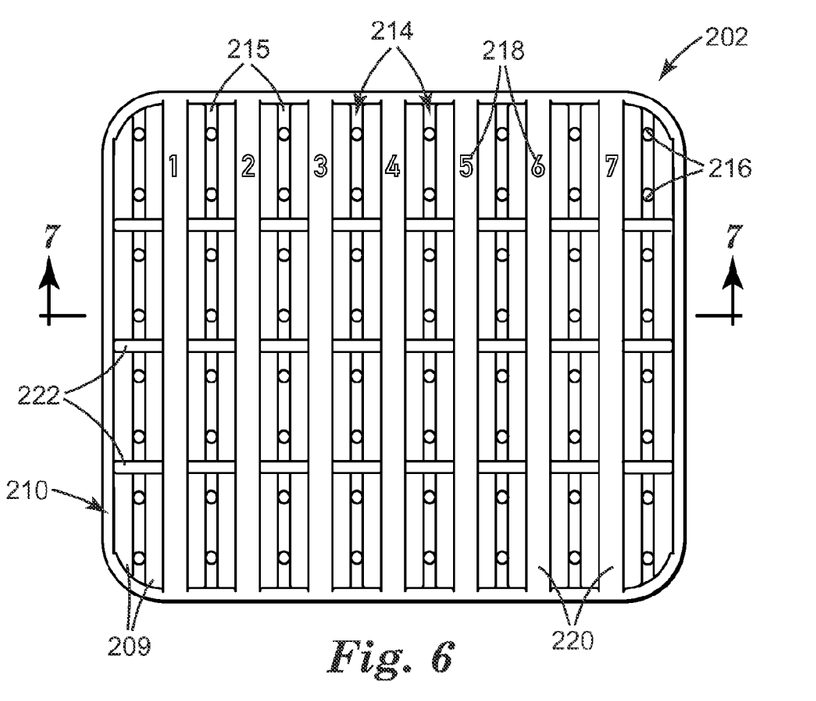
FIG. 6 is a top view of the sintering support of FIG. 5.
Figure 7:
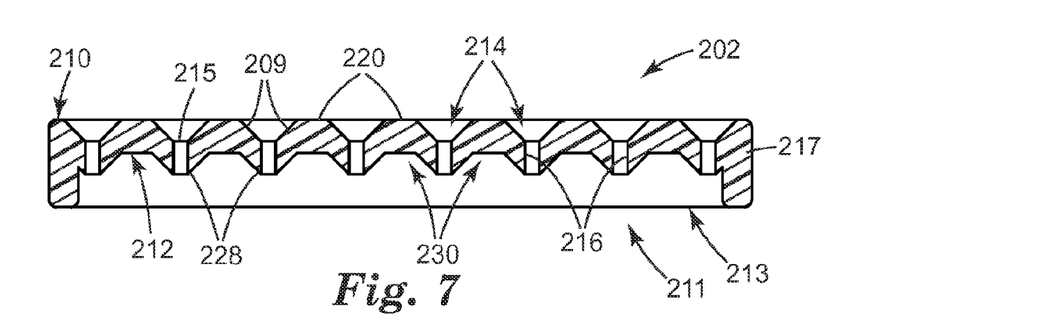
FIG. 7 is a cross-sectional side view of the sintering support of FIGS. 5-6, taken along line 7-7 of FIG. 6.

FIGS. 5-7 illustrate a sintering system 200 according to another embodiment of the present disclosure, wherein like numerals represent like elements. The sintering system 200 shares many of the same elements and features described above with reference to the illustrated embodiment of FIGS. 1-4. Accordingly, elements and features corresponding to elements and features in the illustrated embodiment of FIGS. 1-4 are provided with the same reference numerals in the 200 series. Reference is made to the description above accompanying FIGS. 1-4 for a more complete description of the features and elements (and alternatives to such features and elements) of the embodiment illustrated in FIGS. 5-7.

As shown in FIG. 5, the sintering system 200 can include a sintering support or tray 202 (and particularly, a monolithic sintering support 202, and more particularly, a monolithic ceramic sintering support 202), and one or more dental restorations 204 (and particularly, ceramic dental restorations 204) positioned on the sintering support 202. FIGS. 6-7 illustrate alternate views of the sintering support 202.

As shown in FIGS. 5-7, and with particular reference to FIG. 7, the sintering support 202 includes a first, top surface 210, and a second, bottom surface 212. Similar to the second surface 112 described above and illustrated in FIGS. 1-4, the second surface 212 includes a raised or recessed portion, or has a generally concave shape, such that the sintering support 202 (and the second surface 212) includes an inner portion 211 that is raised relative to an outer portion 213. The outer portion 213 includes a flange 217 that extends downwardly relative to the inner portion 211 and which defines the lowermost portion of the second surface 212. In addition, the sintering support 202 includes one or more recesses 214, such that at least a portion of the first surface 210 is defined by the one or more recesses 214. In some embodiments, as shown in FIGS. 5-7, each recess 214 can be defined by one or more sidewalls 209 and a base 215.

By way of example only, the sintering support 202 illustrated in FIGS. 5-7 has a generally rectangular shape with radiused corners, such that the recesses 214 positioned adjacent the corners are also radiused. The sintering support 202 has a length and a width, and the length is longer than the width. The sintering support 202 includes 32 recesses, arranged in four rows of eight (or said in another way, eight rows of four). However, it should be understood that a variety of sintering support shapes (e.g., square, triangular, polygonal, etc.) can be employed and that a variety of numbers and arrangements of recesses 214 are possible and within the scope of the present disclosure. The number and arrangement of the recesses 214 can depend, at least in part, on the size, shape, and material makeup of the dental restorations 204 to be sintered, the type of sintering furnace used, and the like. The recesses 214 can be sized and arranged to accommodate a variety of dental restorations. For example, a bridge is shown by way of example only as being positioned on the sintering support 202 in such a way that it spans multiple recesses 214.

By way of further example, the recesses 214 illustrated in FIGS. 5-7 generally extend along the width of the sintering support 202, and each recess 214 is separated from an adjacent recess 214 by a major separating wall 220 or a minor separating wall 222. As shown in FIGS. 5-7, and particularly in FIG. 7, the top surfaces, respectively, of the major separating walls 220 and the minor separating walls 222 can define at least a portion of the first surface 210 of the sintering support 202. As shown in FIGS. 5 and 6, the major separating walls 220 can also provide a substrate or surface for recess identifications 218. Alternatively, or in addition, in some embodiments, the minor separating walls 222 can provide a substrate or surface for recess identifications 218.

As mentioned above, in some embodiments, each recess 214 can be defined by two angled sidewalls 209 and a flat base 215. As a result, in some embodiments, each recess 214 can include a truncated V cross-sectional shape, and a width that varies with the depth of the recess 214. In the embodiment illustrated in FIGS. 5-7, each recess 214 is widest at its top, decreases as the depth of each recess 214 increases, and is narrowest at its base 215.

In some embodiments, as shown in FIG. 7, the sintering support 202 can further include one or more downwardly-projecting walls, ribs, or protrusions 228 that correspond to the base(s) 215 of the recess(es) 214. In addition, each downwardly-projecting wall 228 is shown as being separated by one or more upwardly-extending recesses 230, each of which corresponds to the position of a major separating wall 220. The recesses 214 and walls 220 define at least a portion of the first surface 210 of the sintering support 202, and the walls 228 and recesses 230 define at least a portion of the second surface 212, and particularly at least a portion of the inner portion 211 of the second surface 212. In addition, in some embodiments, the sintering support 202 includes additional downwardly-extending walls that correspond to each of the minor separating walls 222, and which further define at least a portion of the second surface 212.

As shown in FIGS. 5-7, in some embodiments, the sintering support 202 can include one or more apertures 216 positioned to provide fluid communication between the first surface 210 and the second surface 212.

The embodiments illustrated in FIGS. 1-7 are shown by way of example only. However, it should be understood that not every embodiment of the sintering support or the sintering support system includes every feature described above and illustrated in FIGS. 1-7. For example, in some embodiments, the sintering support does not include a raised inner portion 111, 211, and in some embodiments, the sintering support does not include any apertures 116, 216 providing fluid communication between the first surface 110, 210 and the second surface 112, 212. Furthermore, in some embodiments, the second surface 112, 212 or the inner portion 111, 211 thereof, can be flat and need not be defined by the walls 128, 228 and recesses 130, 230.

In use, dental restorations (such as the dental restorations 104 and 204 shown in FIGS. 1 and 5 and described above) can be formed according to the following process. First, one or more dental restorations can be provided. Providing a dental restoration can include scanning a patient's mouth to develop a model for the desired dental restoration (e.g., using the LAVA™ system described above), and then forming a dental restoration having the desired shape from an unsintered ceramic (e.g., zirconia) monolith (sometimes referred to as a "blank," e.g., a LAVA™ frame blank). One example of a method that can be used to form the dental restoration is milling. After the monolith, or blank, has been formed into the desired shaped, e.g., by milling, dust can be removed with microbrushes and compressed air to form the unsintered dental restoration.

In some embodiments, the dental restoration can then optionally be shaded or colored to achieve a desired aesthetic. Dental restorations can be colored by a variety of coloring agents to give the desired aesthetics and color to the resulting dental restoration. The coloring agent can be adapted to change the color of the dental restoration after treatment of the dental restoration with the coloring agent, or after a firing or sintering step of the treated dental restoration. For example, in some embodiments, the coloring agent is a coloring solution that includes ions that can be doped in the ceramic crystal structure of the dental restoration during sintering. A variety of coloring agents (e.g., coloring solutions) can be used to color the dental restoration, including, but not limited to, metal-ion-containing solutions, ionic or complex-containing solutions (e.g., those disclosed in Suttor et al., U.S. Pat. No. 6,709,694), other suitable coloring agents, and combinations thereof. By way example only, in some embodiments, coloring solutions comprising a solvent, a coloring agent comprising metal ions, and a complexing agent can be used, such as those described in Schechner et al., PCT Publication No. WO 2008/098157. By way of further example, in some embodiments, coloring solutions comprising a solvent, a metal salt and polyethylene glycol having a $M_n$ in the range of 1,000 to 200,000 can be used, such as those described in Hauptmann et al., US Patent Application Publication No. 2006/0117989.

Dental restorations can be colored or shaded in a variety of ways, including incorporating pigments into the dental restoration ceramic material and/or applying coloring agents (e.g., coloring solutions) to the dental restoration. A coloring agent (e.g., a coloring solution) can be applied to the pre-sintered or absorbent dental restoration in a variety of ways, including at least one of the following: (1) immersion of the dental restoration in coloring solutions of defined concentrations (e.g., for about 2 minutes); (2) deposition of coloring agents to the dental restoration by means of suitable application instruments, such as a brush, swab, or the like; (3) deposition of coloring agents to the ceramic by means of a spraying process; and combinations thereof. Any excessively adhering coloring agent can be removed from the dental restoration with an absorbent paper.

A dental restoration can be characterized as "homogeneously colored" if no color spots can be identified with the human eye on the surface of the dental restoration after the sintering process. More precisely, this can be proven using a commercially available Hunter Lab System. The homogeneity can be measured according to DIN 5033 Measurement of Colours; Parts 1-8 (Normvalenz-System, L*a*b*-Farbraum nach CIE, 1976); DIN 6174 Farbmetrische Bestimmung von Farbabstanden bei Körperfarben nach der CIE-LAB-Formel; DIN 55981 (ISO 787-25) Farbabstandsbestimmung ΔE* using standard operating procedures according to the manufacturer's operation manual (Hunter Lab., Corp.) to determine the sample dimension, the calibration and measurement procedure. Further information regarding this measuring system can also be found in DE 100 52 203 A1 on page 3, line 56 to page 4, line 6 (corresponding to U.S. Pat. No. 6,756,421, col. 4, lines 26-55).

Following the optional shading process, the dental restoration can be dried to allow any water or solvent from the coloring agent (e.g., coloring solution) to evaporate from the outer surface of the dental restoration. Drying can include air drying or drying at elevated temperatures, for example, that are less than 100° C. During the drying process of a shaded dental restoration, ions from the coloring agent can be transported to the outer surface of the dental restoration. In some existing systems, if the drying process is hindered at contact points (e.g., between the dental restoration and a support or surface on which the dental restoration is positioned), a non-uniform color can be observed after sintering. The sintering support 102, 202 of the present disclosure, however, successfully reduces or eliminates any decoloration or discoloration of the dental restoration, as shown and described below in Example 2. In some embodiments, the dental restoration can be air dried by positioning the dental restoration on the sintering support and placing the sintering support and dental restoration in the furnace that will be used for sintering, without turning on the furnace or activating the heat. In some embodiments, the dental restoration can be air dried for at least about 2 hours prior to sintering, in some embodiments, at least about 3 hours prior to sintering, and in some embodiments, at least about 3.5 hours prior to sintering. Dental restorations that have not been shaded generally do not need to be dried prior to sintering.

A sintering support (such as the sintering supports 102 and 202 shown in FIGS. 1-4 and 5-7 and described above) can be provided by any of the above-described methods. The dental restoration can be positioned on the sintering support in preparation for sintering (and, optionally, for drying, if the dental restoration is shaded). The dental restoration can be positioned on the sintering support in a variety of manners, as shown in FIGS. 1 and 5 and as mentioned above, depending on the shape, size, structure and material makeup of the dental restoration. For example, in some embodiments, the dental restoration can be positioned in direct contact with a surface (e.g., the first surface 110 or 210) of the sintering support. In some embodiments, the surface can be defined by one or more recesses (e.g., recesses 114 or 214), such that the dental restoration is positioned in direct contact with one or more recesses of the sintering support. Furthermore, in some embodiments, the recesses can include or be defined by one or more sidewalls and/or a base, and in some embodiments, the dental restoration can be positioned on the sintering support such that the dental restoration is positioned in direct contact with at least one of the sidewalls and base of the recess (or a surface of the sintering support that is at least partially defined by at least one of the sidewalls and the base of the recess). In addition, in embodiments in which the dental restoration is positioned in a recess of the sintering support, the dental restoration can span more than one recess, or in some embodiments, the dental restoration can fit within one recess.

In some embodiments, the dental restoration can be positioned on the sintering support prior to being positioned within a sintering furnace, such that the dental restoration and the sintering support together form a temporary composite, intermediate, or system (such as the system 100 and 200 shown in FIGS. 1 and 5, respectively) that can then be handled together and positioned for sintering.

The dental restoration can be sintered, for example, by placing the dental restoration and sintering support in a furnace, such as the furnace available under the trade designation LAVA™ Therm furnace or LAVA™ Furnace 200, available from 3M ESPE AG, Seefeld, Germany. In some embodiments, the dental restoration can be sintered according to the sintering process recommended by the furnace manufacturer. For example, in some embodiments, the dental restoration can be subjected to a sintering process recommended by 3M ESPE AG, for example, with a temperature cycle of room temperature (e.g., about 25° C.) to a final sintering temperature in the range of 1300° C. to 1650° C. (e.g., 1500° C.), with a heating rate of, e.g., 10 K/min., while being supported on a sintering support of the present disclosure.

Following the sintering process, the dental restoration can be allowed to cool (e.g., within or outside the furnace), and measurements can be made to determine how well the sintered dental restoration corresponds to the desired physical dimensions and aesthetics.

As mentioned above, it is important in sintering dental restorations that the dental restorations not become sintered to one another or to any substrate or surface with which the dental restorations are in contact during sintering. Such adherences can inhibit uniform shrinkage in the dental restoration during shrinkage, which can distort the dental restoration from its desired shape. Such defects generally render the dental restoration unusable.

Such a distortion can be referred to as a "sintering deformation," which can refer to the change of the geometrical shape of a dental ceramic restoration. Such a sintering deformation can occur during the sintering process and can in one, two, or three dimensions. The sintering deformation can be measured to compare the shape of the dental restoration before and after a sintering process. The difference in shape can either be measured by an accurate geometrical measurement of the dental restoration using, for example, a microscope, and/or by examining the precision fit of a dental restoration on a model, as described below.

One exemplary test that can be used for evaluating the deformation of a dental restoration after sintering is as follows: A rod-shaped sample is processed similar to a LAVA™ bridge (milling, dyeing and sintering) with commercially available LAVA™ equipment. The presintered dental restoration (LAVA™ Frame blank for bridges) is milled, thereafter the dust is removed with microbrushes and compressed air. The dental restoration can then optionally be colored according to any of the procedures described above. The dental restoration can then be positioned on the sintering support and sintered. The firing can be done in a LAVA™ Therm furnace with the standard sintering program. After sintering, the deformation of the samples is measured with a profile projector. The term "precision fit" is generally used to refer to the exactness with which a dental restoration fits to a prepared model, e.g., to what extent the internal surface of resulting dental restoration matches the external surface of a tooth structure, such as a prepared tooth stump. Such a precision fit can be especially necessary for wide spanning dental bridges.

In some embodiments, the material makeup, for example, the material purity of the sintering support can affect the adhesions and/or distortions (i.e., uniform shrinkage) of the dental restorations. The sintering supports of the present disclosure are adapted to produce sintered dental restorations with minimal to no adhesions between the dental restoration and the sintering support, and as a result, minimal to no distortions or sintering deformations of the dental restorations, while allowing facile release of the dental restorations from the sintering support. As a result, in some embodiments, the sintering support can be formed of alumina with a purity of at least 97 wt % $Al_2O_3$, in some embodiments, at least 98 wt % $Al_2O_3$, and in some embodiments, at least 99.7 wt % $Al_2O_3$.

In addition, in some embodiments, certain types of contaminants or impurities can affect the adhesions and/or distortions (i.e., uniform shrinkage) of the dental restorations. For example, the present inventors discovered that sintering dental restorations formed of dental grade zirconia (available under the trade designation LAVA™ from 3M ESPE AG, Seefeld, Germany) on an alumina sintering support formed of 96 wt % $Al_2O_3$ and 3-4 wt % silica ($SiO_2$) led to strong adherences between the sintering support and the dental restorations.

In addition, in some embodiments, the material purity of the sintering support can also affect the aesthetics and color of the dental restoration. That is, in some embodiments, certain impurities in the sintering support can cause discoloration of the dental restorations, leading to undesired overall color, colored spots, color inhomogeneity, etc. For example, the present inventors surprisingly discovered that silica caused adhesions and iron impurities in an alumina sintering support caused discoloration of zirconia dental restorations.

For at least the reasons described above, in some embodiments, the sintering support can be configured to include less than 0.5 wt %, and in some embodiments, less than 0.1 wt % of one or more of the following contaminants or impurities: iron, manganese, vanadium, cobalt, copper, nickel, lanthanum, other lanthanoid oxide impurities, other oxide impurities, and combinations thereof.

In some embodiments, the grain size and/or surface roughness of the sintering support can affect the adhesion and distortion of the dental restorations. For example, in some embodiments, a higher grain size and/or higher surface roughness of the sintering support can lead to a sintering support that is less sintering active and which maintains multiple, small area contact points for the dental restorations to allow for uniform air and heat circulation around the dental restoration and provides uniform shrinkage during sintering. However, the present inventors surprisingly and unexpectedly discovered that the relatively high surface roughness would provide contact points for the dental restorations without providing active sintering sites that would create adhesions between the dental restorations and the sintering support during sintering.

In some embodiments, the sintering support has a coarse grain size and has low sintering activity. For example, in some embodiments, the sintering support has a grain size of at least 5 µm, in some embodiments, at least 10 µm, in some embodiments, at least 40 µm, and in some embodiments, at least 80 µm.

In some embodiments, the sintering support has high surface roughness. For example, in some embodiments, the sintering support has a surface roughness parameter, $R_z$, of at least 10 µm (e.g., 60 µm), in some embodiments, at least 80 µm, and in some embodiments, at least 150 µm, as determined according to the following standard test methods: EN ISO 4287:1998-08, ISO 4288:1996-08, and EN ISO 11562/AC: 2008-10.

In some embodiments, the efficiency and/or effectiveness of the sintering process can be affected by the porosity and/or density of the sintering support. That is, in some embodiments, a more porous sintering support can be employed to lower the mass (e.g., to lower the heat capacity per volume) of the sintering support and to require less energy to heat (e.g., uniformly) the sintering support, and to allow the sintering support to cool much more quickly, thereby reducing the overall sintering process time.

Furthermore, in some embodiments, the porosity and/or density of the sintering support can affect the drying and resulting color and aesthetics of shaded dental restorations. In some embodiments, a sintering support that is too dense (i.e., has too low of a porosity) can inhibit adequate evaporation of a solvent from a coloring agent that has been applied to a dental restoration, such that the solvent is not uniformly evaporated from the dental restoration, which can cause ions from the coloring agent to migrate to one or more areas of the dental restoration, creating an uneven colored appearance, colored spots, or the like. Alternatively, or in addition, apertures in the sintering support (e.g., the apertures 116, 216) can also be sized, shaped and/or positioned to promote adequate drying of shaded dental restoration.

In some embodiments, the open porosity and/or density of the sintering support can be determined using a water infiltration method. For example, at least a portion of the sintering support can be infiltrated with water to calculate the open porosity of the ceramic structure, and the density can be determined according to the Archimedes' principle.

In some embodiments, the sintering support has an open porosity of at least 25%, in some embodiments, at least 35%, and in some embodiments, at least 50%.

In some embodiments, the sintering support has a density of at least 25% of the theoretical density, in some embodiments, at least 35% of the theoretical density, and in some embodiments, at least 50% of the theoretical density.

In some embodiments, the sintering support has a density of no greater than 3 $g/cm^3$, in some embodiments, no greater than 2 $g/cm^3$, and in some embodiments, no greater than 1.6 $g/cm^3$.

The following working examples are intended to be illustrative of the present disclosure and not limiting.

EXAMPLES

Example 1

Scanning Electron Microscopy (SEM) Analysis of a Sintering Support

The top surface (e.g., the top surfaces 110 and 210 shown in FIGS. 1-4 and 5-7, respectively) of a sintering support of the present disclosure was investigated using SEM. Scanning electron microscope analyses were carried out with a Leo 1530 VP FE-SEM instrument, available from (Carl Zeiss SMT AG, formerly Leo Elektronenmikroskopie GmbH, Germany). The top surface of the sintering support that was investigated was the surface that would contact dental restorations during a sintering process. The sintering support was formed of a porous alumina (available under the trade designation MA 3.6 from Werkstoffzentrum Rheinbach GmbH, Germany) with 99.7 wt % alumina having an open porosity of 33%, a closed porosity of 20%, and a density of 1.85 $g/cm^3$.

Figure 8:
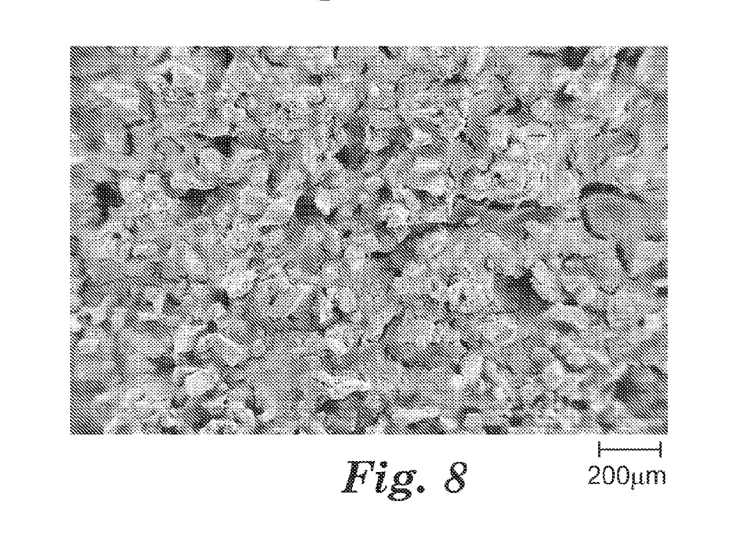
FIG. 8 is a scanning electron micrograph of a sintering support according to one embodiment of the present disclosure, taken at a magnification of 100×, according to Example 1.
Figure 9:
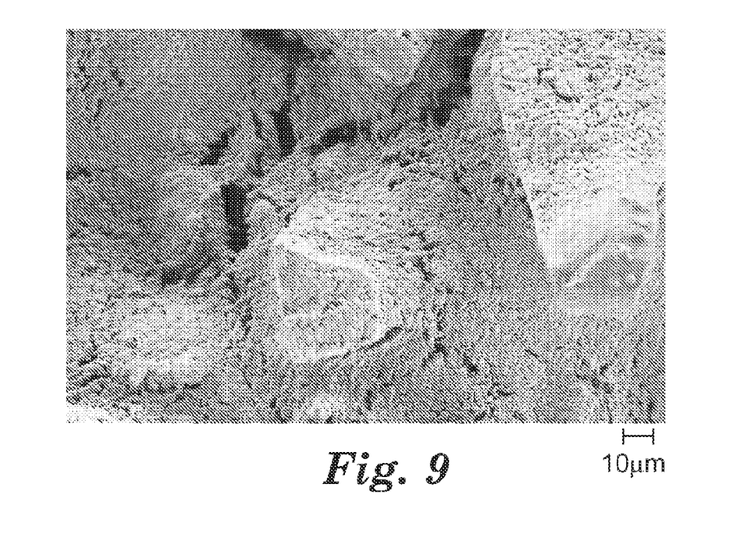
FIG. 9 is a scanning electron micrograph of the sintering support of FIG. 8, taken at a magnification of 1000×, according to Example 1.

The results of the SEM analysis of the top surface of the sintering support at a magnification of 100× is shown in FIG. 8, and the results of the SEM analysis of the same surface of the sintering support at a magnification of 1000× is shown in FIG. 9. The results of the SEM analysis showed biomodal alumina grain sizes with large well-developed hexagonal shaped crystals with a length of up to 150 μm, and a finer grain structure of up to 5 μm. The SEM results also showed relatively large gaps, pores, and high surface roughness, with contact points that protrude out of the sintering support ceramic microstructure.

Example 2

Decoloration Analysis of Shaded Restorations

Pressed and presintered zirconia discs with a diameter of 24 mm and a thickness of 2 mm, available under the trade designation LAVA™ zirconia from 3M ESPE AG, Seefeld, Germany were shaded with a coloring solution available under the trade designation LAVA™ Frame Shading Liquid FS4 from 3M ESPE AG by immersing the zirconia discs in the coloring solution for 2 minutes to form shaded zirconia discs. After removal, excess coloring solution was carefully removed with a clammy fabric and the discs were placed on the sintering support. The shaded zirconia discs were then sintered according to each of the following three sintering methods:

(1) Without contact—the shaded zirconia discs were placed on thin alumina rods having almost no contact points (represented as "Without contact" in FIG. 10), (2) Porous alumina—the shaded zirconia discs were placed with one side in direct contact with a porous alumina plate (represented as "Porous alumina" in FIG. 10), available under the trade designation MA 3.6, Werkstoffzentrum Rheinbach GmbH, Germany (i.e., having the material makeup and properties specified in Example 1 above), representing a surface of a sintering support of the present disclosure, and (3) Dense alumina—the shaded zirconia discs were placed with one side in direct contact with a 75 mm×50 mm×4 mm rectangular dense alumina plate comprising 99.7% $Al_2O_3$ (represented as "Dense alumina" in FIG. 10), available under the trade designation ALSINT 99.7 from W. Haldenwanger Technishce Keramik GmbH & Co. KG, Germany.

Figure 10:
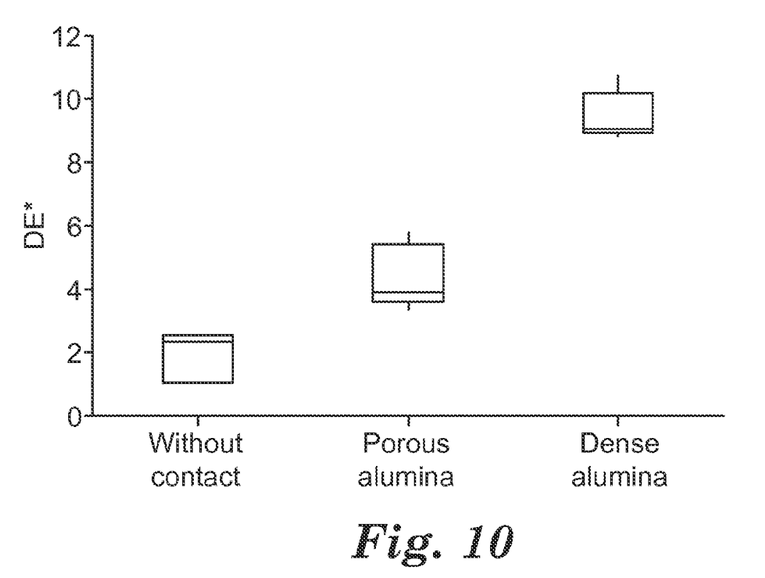
FIG. 10 is a graph of decoloration of shaded zirconia discs, according to Example 2.

The Delta E (DE*) value was calculated from the color difference of the upper side in comparison to the bottom side of each zirconia disc. A large DE* value indicated a strong color difference between both sides. No visible decoloration was observed on the zirconia discs sintered on thin alumina rods without contact areas, and slight to medium decolorations were observed on samples sintered in contact with the porous alumina surface. However, strong decoloration was noticeable on the bottom side of the samples sintered in contact with the dense alumina plate. The DE* value results for the three different scenarios are shown in FIG. 10. The DE* value gives the differences between two colors in a three-dimensional color coordinate space, and is calculated from CIELAB color measurements (i.e., the color space specified by the International Commission on Illumination (Commission Internationale d'Eclairage) according to the following equation:

$$\Delta E = \sqrt{(\Delta L^*)^2 + (\Delta a^*) + (\Delta b^*)^2}$$

where L* represents the lightness of the color (i.e., L*=0 yields black and L*=100 indicates diffuse white; specular white may be higher), a* represents its position between red/magenta and green (i.e., negative values indicate green while positive values indicate magenta), and b* represents its position between yellow and blue (i.e., negative values indicate blue and positive values indicate yellow).

Example 3

Fit of Dental Restorations Sintered on a Sintering Support

Test Method—Rating of Fit of Sintered Dental Restorations to Model

The sintered dental restorations were each fit with light pressure onto the matching model, i.e., a saw cut model of a patient's mouth situation. The fit of the sintered dental restorations on the model were observed using stereo microscope with a 10× magnification without any other auxiliary equipment.

The degree of fit of each finished dental ceramic restoration was rated according to the criteria listed in Table 1:

TABLE 1

Fit Rating and Criteria for Dental Restorations

| FIT RATING | CRITERIA |
|---|---|
| 5 | No reworking required |
|   | nearly excellent fit to excellent fit over the complete margin |
|   | no grinding necessary |
| 4 | Minimal adjustment required |
|   | some gaps over the complete margin |
|   | 70-80% of the margin without gaps |
|   | nearly excellent fit to excellent fit over the single copings |
|   | slight rocking at the occlusal surface is removable by grinding |
| 3 | Fit only after considerable grinding correction |
|   | 30-50% of the margin with gap |
|   | some gaps cannot removed by grinding |
|   | slight rocking at the occlusal surface also after grinding |
| 2 | No fit possible |
|   | gaps over 200 μm |
|   | extremely rocking possible |
| 1 | No fit possible |
|   | restoration totally rocked |
|   | gaps over 300 μm |
|   | extremely rocking possible |

Figure 11:
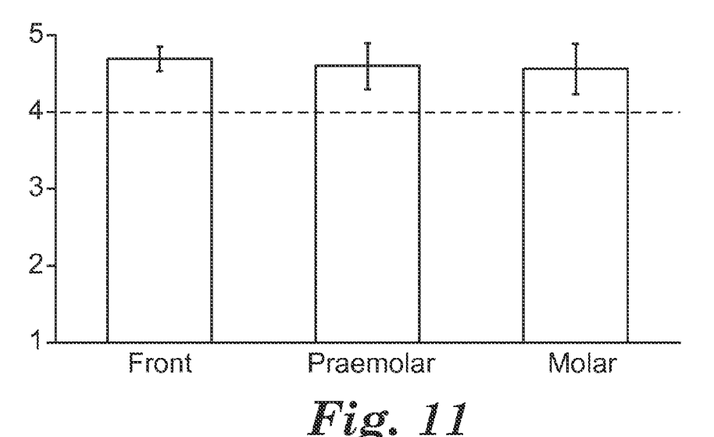
FIG. 11 is a graph of fit ratings of dental restorations sintered on a sintering support according to one embodiment of the present disclosure, according to Example 3.
Figure 12:
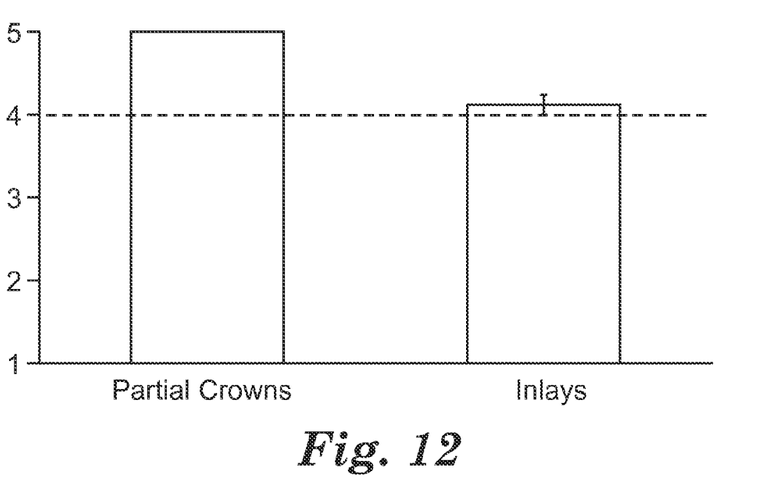
FIG. 12 is a graph of fit ratings of dental restorations sintered on a sintering support according to one embodiment of the present disclosure, according to Example 3.

Zirconia crowns (i.e., represented as "Front" crowns, "Praemolar" crowns, and "Molar" crowns in FIG. 11), partial crowns and abutments (i.e., represented as "Inlays" in FIG. 12) milled from LAVA™ Frame zirconia (available from 3M ESPE AG) were sintered directly on an alumina sintering support of the present disclosure comprising alumina available under the trade designation MA 3.6 from Werkstoffzentrum Rheinbach, GmbH, Germany (and having the material makeup and properties specified in Example 1) at 1500° C. for 120 min. dwell time. The fit of each sintered crown, partial crown, and abutment was then tested according to the above-described 'Rating of Fit' test method. As shown in FIGS. 11 and 12, all of the sintered dental restorations that were tested exceeded the acceptance criteria of a fit rating of 4.

Example 4

Energy Dispersive X-Ray Analysis (EDX) of a Sintering Support

An alumina sintering support of the present disclosure was provided comprising alumina available under the trade designation MA 3.6 from Werkstoffzentrum Rheinbach, GmbH, Germany (and having the material makeup and properties specified in Example 1).

The alumina sintering support was analyzed with EDX using a Leo 1530 VP FE-SEM EDX Detector Oxford Inca instrument, available from Oxford Instruments, UK. The results of the EDX analysis performed at 25 kV for 360 s showed that the alumina sintering support comprised $Al_2O_3$ with no additional elements that could be detected by EDX.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A method for sintering dental restorations, the method comprising:
    providing a monolithic sintering support having an open porosity of at least 25% and comprising a surface;
    positioning a dental restoration in direct contact with the surface, wherein the dental restoration is shaded; and
    sintering the dental restoration while the dental restoration is in direct contact with the surface of the monolithic sintering support to form a sintered dental restoration,
    wherein the surface is defined at least partially by a recess, and wherein positioning a dental restoration in direct contact with the surface includes positioning a dental restoration at least partially in the recess.

2. The method of claim 1, wherein the recess includes a channel that extends along a length of the monolithic sintering support.

3. The method of claim 1, wherein positioning a dental restoration at least partially in the recess includes positioning a dental restoration in more than one recess.

4. The method of claim 1, wherein the recess includes a truncated V cross-sectional shape.

5. The method of claim 1, further comprising:
    providing an unsintered zirconia monolith; and
    milling the zirconia monolith to form the dental restoration.

6. The method of claim 1, wherein the monolithic sintering support comprises alumina.

7. The method of claim 1, wherein the monolithic sintering support comprises zirconia.

8. The method of claim 1, wherein the dental restoration comprises zirconia.

9. The method of claim 1, wherein the monolithic sintering support comprises at least 97 wt % alumina.

10. The method of claim 1, wherein the monolithic sintering support has a porosity of at least 35%.

11. The method of claim 1, wherein the monolithic sintering support has a density ranging from about 1.6 $g/cm^3$ to about 3 $g/cm^3$.

12. The method of claim 1, wherein the monolithic sintering support has a density of about 1.8 $g/cm^3$.

13. The method of claim 1, wherein the monolithic sintering support has an average grain size of at least 5 μm.

14. The method of claim 1, wherein the monolithic sintering support comprises less than 0.5 wt % of at least one of the following impurities: iron, manganese, vanadium, cobalt, copper, nickel, oxide impurities, and combinations thereof.

15. The method of claim 1, wherein the monolithic sintering support includes an indexing system, and further comprising indexing the location of the dental restoration on the monolithic sintering support.

16. The method of claim 1, wherein the monolithic sintering support includes a plurality of apertures positioned to provide fluid communication between a first major surface of the monolithic sintering support and a second major surface of the monolithic sintering support.

17. The method of claim 1, wherein the sintered dental restoration has a fit rating of at least 4.

18. The method of claim 1, wherein the sintered dental restoration has a decoloration DE value of no greater than 6.

19. A system for sintering dental restorations, the system comprising:
    a monolithic sintering support having an open porosity of at least 25% and comprising a surface, wherein the surface is defined at least partially by a recess;
    a dental restoration positioned in direct contact with the surface, such that the dental restoration is positioned at least partially in the recess, wherein the dental restoration is shaded.

20. The system of claim 19, wherein the monolithic sintering support comprises at least 97 wt % alumina.

* * * * *

UNITED STATES PATENT AND TRADEMARK OFFICE
CERTIFICATE OF CORRECTION

Page 1 of 1

PATENT NO.         : 8,834,751 B2
APPLICATION NO.    : 13/147614
DATED              : September 16, 2014
INVENTOR(S)        : Rainer Dittmann et al.

It is certified that error appears in the above-identified patent and that said Letters Patent is hereby corrected as shown below:

In the Specification

Column 14
Line 66, Delete "biomodal" and insert -- bimodal --, therefor.

Column 15
Line 40, Delete "Technishce" and insert -- Technische --, therefor.

Column 16
Line 65, Delete "Reinbach," and insert -- Rheinbach, --, therefor.

Signed and Sealed this
Seventeenth Day of February, 2015

Michelle K. Lee
*Deputy Director of the United States Patent and Trademark Office*